United States Patent [19]
Young

[11] Patent Number: 5,559,033
[45] Date of Patent: Sep. 24, 1996

[54] METHOD AND APPARATUS FOR CLOSED LOOP AIR CIRCULATION COMPOSTING WITH AN EXTERNAL AIR MANIFOLD

[75] Inventor: Richard N. Young, Atlanta, Ga.

[73] Assignee: DBS Manufacturing, Inc., Forest Park, Ga.

[21] Appl. No.: 534,153

[22] Filed: Sep. 26, 1995

Related U.S. Application Data

[63] Continuation-in-part of Ser. No. 323,451, Oct. 14, 1994.
[51] Int. Cl.$^6$ .................................................. C12M 1/10
[52] U.S. Cl. ................................ 435/290.3; 435/290.4
[58] Field of Search ........................... 435/290.1, 290.2, 435/290.3, 290.4; 71/12–14, 25

[56] References Cited

U.S. PATENT DOCUMENTS

| | | | |
|---|---|---|---|
| 2,948,593 | 8/1960 | Larson | 435/298.2 |
| 4,493,770 | 1/1985 | Moilliet | 210/603 |
| 5,145,581 | 9/1992 | Novy et al. | 210/609 |
| 5,169,782 | 12/1992 | Murphy et al. | 435/312 |
| 5,292,637 | 3/1994 | Bohnensieker | 435/3 |
| 5,427,947 | 6/1995 | Dalos | 435/298.2 |

FOREIGN PATENT DOCUMENTS

| | | |
|---|---|---|
| 1226-786-A | 9/1989 | Japan. |
| 0870785 | 6/1961 | United Kingdom. |

*Primary Examiner*—David A. Redding
*Attorney, Agent, or Firm*—Needle & Rosenberg, P.C.

[57] ABSTRACT

An apparatus for biologically decomposing a material, comprising a frame and a substantially airtight housing rotatably mounted on the frame is disclosed. The housing has a first outside surface and a first inside surface, a first end and a second end, the first inside surface defining an enclosure therein. The housing also defines a plurality of openings therethrough. A first air header supplies air to, and a second air header removes air from, a plurality of air manifolds disposed external to the housing and in fluid communication with the enclosure through the openings defined by the housing. The plurality of air manifolds includes a first plurality of air manifolds in fluid communication with the first air header and a second plurality of air manifolds in fluid communication with the second air header. Air passes from the first air header through the first plurality of air manifolds into the enclosure and passes out of the enclosure through the second plurality of manifolds to the second air header.

17 Claims, 7 Drawing Sheets

METHOD AND APPARATUS FOR CLOSED LOOP AIR CIRCULATION COMPOSTING WITH AN EXTERNAL AIR MANIFOLD

CROSS REFERENCE TO A RELATED APPLICATION

This application is a continuation-in-part of application Ser. No. 08/323,451, filed on Oct. 14, 1994.

BACKGROUND OF THE INVENTION

1. Field of the Invention

This invention relates to a method and apparatus for composting. More particularly, this invention relates to continuous and cost-effective composting of large quantities of waste material while maintaining maximum control over the reaction parameters by using closed loop air circulation with an external air manifold.

2. The Prior Art

General methods and apparatuses for composting have existed many years. Composting may even be accomplished without any particular apparatus at all. For instance, windrows can be used. Windrows is the composting of a material by laying it out on a field and periodically turning it over with a tractor However, windrows suffer from a number of deficiencies. First, windrows are highly susceptible to adverse weather conditions. Furthermore, the biological and chemical makeup of the material to be composted cannot be assayed and used to adjust the composting parameters. Mixing of the windrowed material may only be accomplished by manually overturning the windrows. Manual overturning often leaves partially composted material in a non-homogenous state. This non-homogeneity leads to non-uniform temperature distribution as well as anaerobic pockets in the material. These pockets create the obnoxious odors associated with open-air composting methods. Therefore, a need exists for an improved composting method which overcomes the deficiencies of windrowing.

Converting sewage sludge into usable humus fertilizer is an environmentally sound goal. This conversion is accomplished via aerobic stabilization and rotting, i.e., composting. In actual use, static methods of composting (such as windrowing) remain unsatifactory on both the technical and economic level. The dissatisfaction has lead to efforts to develop machine composting.

Since the 1970s, composting has become an important method for stabilizing and processing municipal sewage. See EPA, *Summary Report on In-Vessel Composting of Municipal Wastewater Sludge,* Risk Reduction Engineering Laboratory, Center for Environmental Research Information, September 1989. The technology has developed extremely rapidly, from less than 10 facilities in 1975 to nearly 200 under design or in operation in 1989. Because of odor, labor, and materials-handling problems, designers are producing composting systems built to contain the materials within a vessel. Municipalities continue to face serious problems in dealing with odors, removing moisture, handling the materials in the system and marketing the product.

A general composting process begins with the mixing of sludge cake, amendment, if any, (e.g., sawdust) and recycling it in an aerated reactor. Air is diffused into the reactor for temperature control, moisture removal and biological metabolism. Air from within the reactor is then exhausted to an odor treatment system before being dispersed into the atmosphere. After a desired detention time within the vessel, the material is removed from the reactor for further curing/storage.

Composting occurs in multiple stages. The first stage is a high-rate phase. This phase is characterized by high oxygen uptake rates, high temperatures, rapid degradation of biodegradable volatile solids and high odor production. The second stage is a curing phase. This phase is characterized by lower temperatures, reduced oxygen uptake rates and a lower, but significant, potential for odor production.

In machine composting methods, the user can control mixing, ventilation, oxygen supply, moisture content and temperature to more reliably, rapidly and economically transit the two phases and, therefore, perform composting. As noted above with respect to windrows, the major problem with composting is the formation of anaerobic zones as a result of insufficient mixing. Despite numerous efforts, none of the existing machine solutions provides a truly simple, economical, elegant solution to the general problems associated with composting.

Other in-vessel composting apparatuses solve, at least to some degree, some of the problems of windrowing. Salvageable materials in the municipal waste are manually, pneumatically, mechanically, or electromagnetically removed. The remainder is comminuted and any paper and film plastic is removed and burned. The heat from burning is used to evaporate water from the sewage sludge or for drying the compost. The remaining waste is then deposited in a series of ½" thick layers in a composting tank. Sewage sludge is added. Oxygen-enriched air is introduced through a false bottom to accelerate aeration. An agitator is used to mix the compost and accelerate decomposition. The compost is finally dried with hot air, ground, and bagged as fertilizer. However, such devices do not use a rotating vessel. The lack of rotation of the entire vessel necessitates the use of an external agitator. The likelihood of anaerobic pockets is substantial. Furthermore, it is unlikely that homogenous aeration will occur considering the density of partially composted materials.

Some in-vessel composters employ air tubes extending radially from a central axis inside of a vessel, thereby delivering air to the periphery of the enclosure as the vessel rotates. Because the tubes encounter resistance from the material being composted, they must be made of stainless steel, or other strong and expensive materials. Such composters have the disadvantage of the tubes breaking when forced against large clumps of compost, which then requires time consuming and expensive repairs.

SUMMARY OF THE INVENTION

The above-noted disadvantages of the prior art are overcome by the present invention, a reaction vessel for biologically decomposing a material.

One aspect of the invention is an apparatus for biologically decomposing a material, comprising a frame and a substantially airtight housing rotatably mounted on the frame. The housing defines an enclosure therein. The housing also defines a plurality of openings therethrough. A first air header supplies air to, and a second air header removes air from, a plurality of air manifolds disposed external to the housing and in fluid communication with the enclosure through the openings defined by the housing. The plurality of air manifolds includes a first plurality of air manifolds in fluid communication with the first air header and a second plurality of air manifolds in fluid communication with the second air header. Air passes from the first air header through the first plurality of air manifolds into the enclosure and passes out of the enclosure through the second plurality of manifolds to the second air header.

Another aspect of the invention is an apparatus for biologically decomposing a material, comprising a frame and a substantially airtight housing rotatably mounted on the frame. The housing has a first outside surface and a first inside surface, the first inside surface defines an enclosure therein. The housing also has a first end defining a first aperture for receiving the material into the enclosure and a second end defining a second aperture for discharging the material from the enclosure. The housing also defines a plurality of openings therethrough. The apparatus also comprises a first air header, a second air header and a plurality of air manifolds disposed external to the housing and in fluid communication with the enclosure through the openings defined by the housing. The plurality of air manifolds includes a first plurality of air manifolds in fluid communication with the first air header, wherein air passes from the first air header through the first plurality of air manifolds into the enclosure, and a second plurality of air manifolds in fluid communication with the second air header, wherein air passes out of the enclosure through the second plurality of manifolds to the second air header. A tubular member extends axially from the first outside surface of the housing and terminates in an end. The tubular member has a second inside surface and a second outside surface and defines a plurality of orifices therethrough spaced apart about the circumference of the tubular member, one of the manifolds extending radially from each of the orifices.

A partitioning member is disposed within the tubular member and has two oppositely disposed upright plates connected by a curved member having a third inside surface and a third outside surface. The curved member is perpendicular to the axis of said housing and the partitioning member defines a second chamber between the third inside surface of the curved member, the two upright plates and the second inside surface of the tubular member. The second chamber is in fluid communication with said second air header. A wall, having a first side and a second side, covers the end of the tubular member with a first chamber being defined by the second side of the wall, the third outside surface of the curved member and the second inside surface of the tubular member, the first chamber being in fluid communication with the first air header.

The first plurality of air manifolds is in fluid communication with the first chamber and the second plurality of air manifolds is in fluid communication with the second chamber, thereby selectively directing fluid flow from the first header through the first plurality of manifolds and selectively directing fluid flow from the second plurality of manifolds through the second header. The ones of the plurality of air manifolds included in the first plurality and the second plurality depends on the rotational position of the housing.

Yet another aspect of the invention is a method of composting a material. The material is placed in a housing and the housing is rotated. Air is injected into the housing through openings in the periphery of the housing as the housing rotates. Air is removed from the housing from openings in the periphery of the housing as the housing rotates. As the material rotates in the housing, biological decomposition of the material takes place so that after the material has reached a predetermined level of decomposition, the material is removed from the housing.

An advantage of the present invention is that it circulates air in the enclosure without requiring internal air tubes.

A further advantage of the present invention is that the air manifolds are external to the enclosure and, therefore, may be constructed of inexpensive materials.

A further advantage of the present invention is that the air manifolds may be easily repaired without having to enter the enclosure.

These and other advantages will become apparent from the following description of the preferred embodiment taken in conjunction with the following drawings, although variations and modifications may be effected without departing from the spirit and scope of the novel concepts of the disclosure.

DETAILED DESCRIPTION OF THE INVENTION

A preferred embodiment of the invention is now described in detail. Referring to the drawings, like numbers indicate like parts throughout the views. As used in the description herein and throughout the claims that follow, "a," "an," and "the" includes plural reference unless the context clearly dictates otherwise. Also, as used in the description herein and throughout the claims that follow, the meaning of "in" includes "in" and "on" unless the context clearly dictates otherwise.

Figure 1:
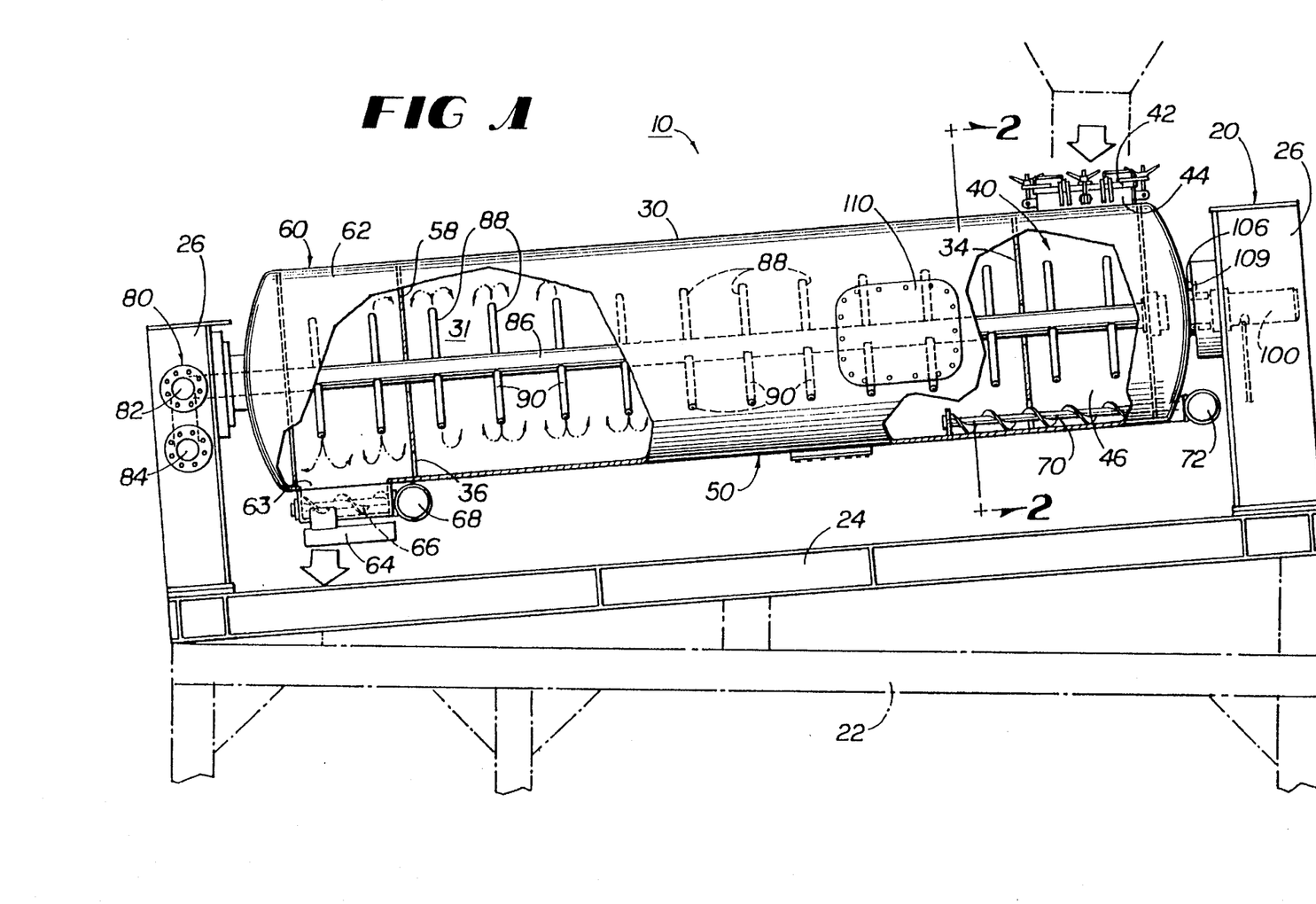
FIG. 1 is a side elevational partial cut-away view of a reaction vessel in accordance with a first embodiment of the invention.

In one preferred embodiment of the invention 10, as shown in FIG. 1, a substantially cylindrical housing 30, defining therein an enclosure 31, is rotatably mounted on a frame 20. The frame 20 has a substantially horizontal sub-frame 22 that supports an inclined portion 24 and two upright support stantions 26. The housing 30 is vertically and laterally supported by a shaft 33 affixed to each side of the housing 30 and journaled into a beating 32 affixed to each of the upright support stantions 26.

Figure 2:
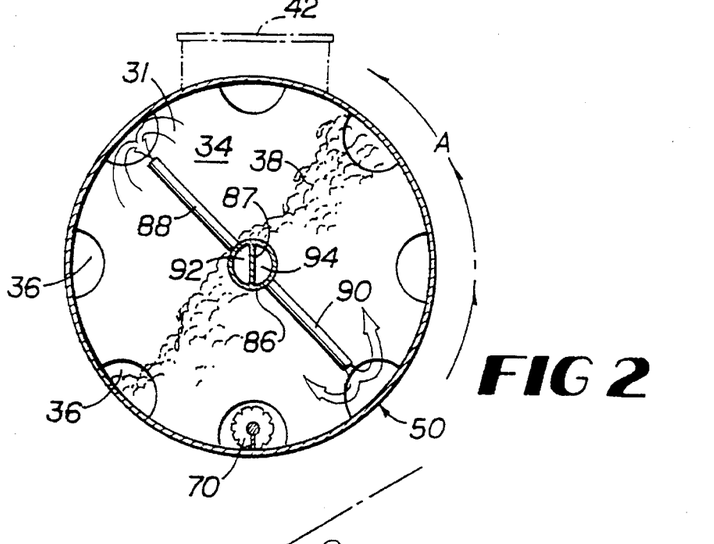
FIG. 2 is a cross sectional view of the first embodiment of the present invention taken along lines 2—2.

The housing 30 has a receiving section 40 which comprises a receiving hatch 42 that opens to a receiving aperture 44 through which material may be introduced into the enclosure 31. If the embodiment is configured for continuous processing, a first wall 34 may be disposed within the enclosure 31, substantially perpendicular to the axis of rotation, thereby defining a receiving chamber 46. Referring to FIG. 2, The wall 34 has a plurality of openings 36 passing through it to allow the material being decomposed 38 to pass out of the receiving chamber 46. A material conveyor also may be used to move material out of the receiving chamber 46. Referring again to FIG. 1, such a material conveyor could comprise a screw auger 70 driven by a motor 72. If the embodiment is configured for processing in the batch mode, the first wall 34 is unnecessary, as the enclosure 31 need have only one chamber.

Disposed within the enclosure 31 is a reaction chamber 50 in which the material to be composted undergoes biological decomposition. In one preferred embodiment, the reaction chamber 50 is disposed between the first wall 34 and a second wall 58. In this embodiment, a discharge section 60 comprises a discharge chamber 62 defined by the second wall 58. Properly decomposed material in the discharge chamber 62 passes through a discharge aperture 63 into a discharge conveyor 66, driven by a motor 68, and through a gate 64 into a container used to carry off the composted material (not shown).

If sewage, or other sticky sludge, is to be treated, some form of comunuter (not shown) should be disposed within the enclosure 31, preferably near to the discharge section, to break up any balls that form in the material. This comunuter could comprise a rotating shaft with a plurality of radial blades extending outward from the shaft.

The rate of decomposition of the material inside the enclosure 31 is controlled by controlling the rotation rate of the housing 30 and the environmental conditions within the enclosure 31. The environmental conditions controlled include: the temperature, the humidity, the oxygen ($O_2$) content of the air, and the carbon dioxide ($CO_2$) content of the air. In some applications, the rate of change of the $CO_2$ level indicates the degree of decomposition. These conditions are controlled by monitoring and modifying air in a closed-loop air system 80 that circulates air within the enclosure 31. In alternate embodiments, other gasses, such as ammonia, hydrogen sulfide and methane, are monitored.

Hydrogen sulfide and methane would be likely by-products of an anaerobic decomposition. If the present invention is used in soil remediation, the process may be started anaerobically and, after the completion of anaerobic decomposition, switched to an aerobic process. Therefore, in such an application, the monitoring of hydrogen sulfide and methane levels would be important.

The air system 80 is maintained as a closed-loop system to prevent the escape of any undesirable gasses. Air entering the enclosure 31 passes through an air introduction flange 82 into a bifurcated supply/return manifold 86 which comprises a pipe divided along its axis by a manifold wall 87. As shown in FIG. 2, the air passes through a supply side 94 of the manifold wall 87 into a plurality of supply pipes 90 where the air is discharged into the enclosure 31 via the pile of material being decomposed 38. The air filters through the material 38 and returns to the manifold 86 through a plurality of return pipes 88 into a return side 92. As shown in FIG. 1, the air then exits the enclosure 31 through an air return flange 84.

The housing 30 is continuously rotated by a motor 100 supported by one of the upright stantions 26 and coupled to the housing 30. The motor 100 may be an electric motor or any suitable device for causing the housing 30 to rotate.

An access and inspection hatch 110 is attached to the housing 30, allowing access for inspection and repair of the system. In some embodiments, this could be a window to allow for continuous inspection of the material. Some embodiments would not require such a hatch 110.

Figure 3:
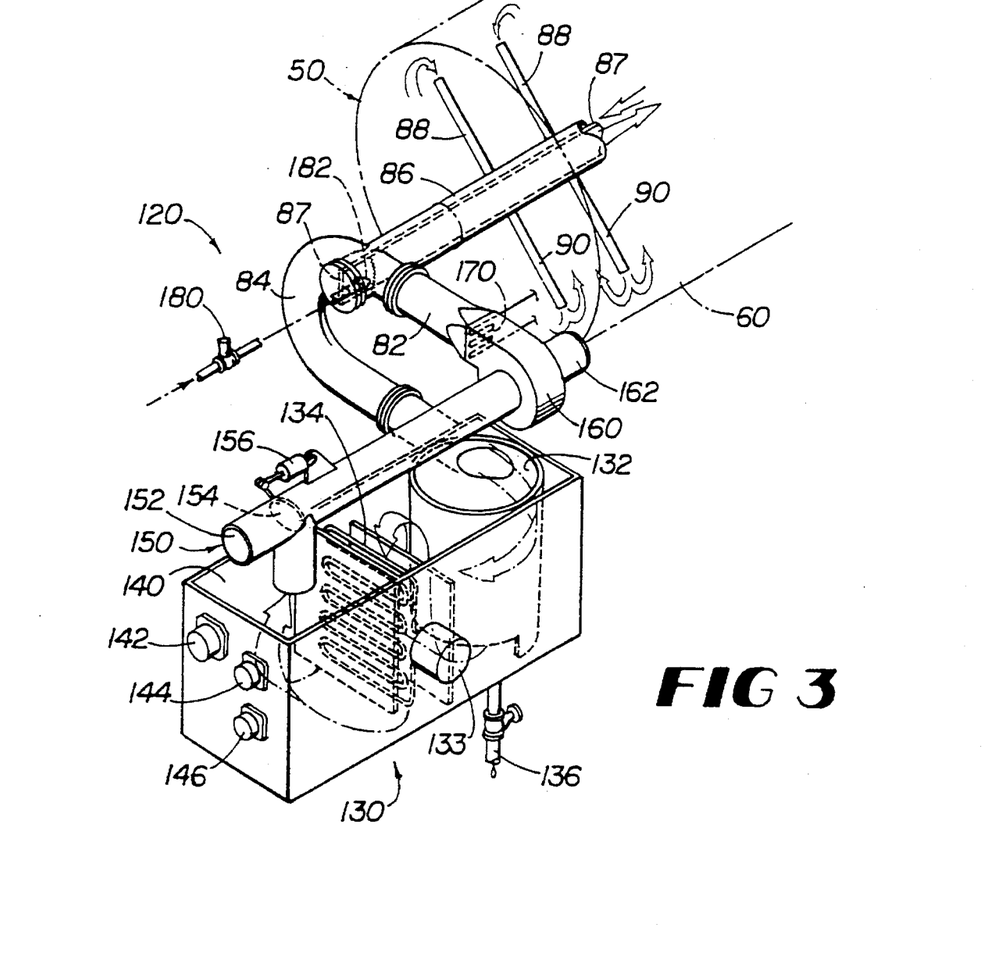
FIG. 3 is a perspective view of one end of the reaction vessel, showing the air flow mechanism and the environmental control means.

Referring to FIG. 3, air exiting the enclosure 31 through the air return flange 84 passes into the air treatment and monitoring plenum 130. In the treatment and monitoring plenum 130, the air first passes through a cyclonic separator drum 132, where any large particles or water droplets are removed from the air as it circulates around the drum 132. The air then passes through a heat exchanger/dehumidifier unit 134, which is capable of both removing heat and condensing water vapor from the air as it cools down. A drain 136 allows condensed water to be removed from the system.

The air then passes through an air sensing chamber 140 where it comes in contact with an $O_2$ sensor 142, a $CO_2$ sensor 144, and a humidity sensor 146. These sensors could comprise remote sensors which generate electronic signals representative of the corresponding sensed values or the they could comprise nonelectronic sensors used in local operation. After passing through the air sensing chamber 140, the air flows into a blower 160 which blows it back into the enclosure 31 through the air introduction flange 82 and the manifold 86.

Figure 4:
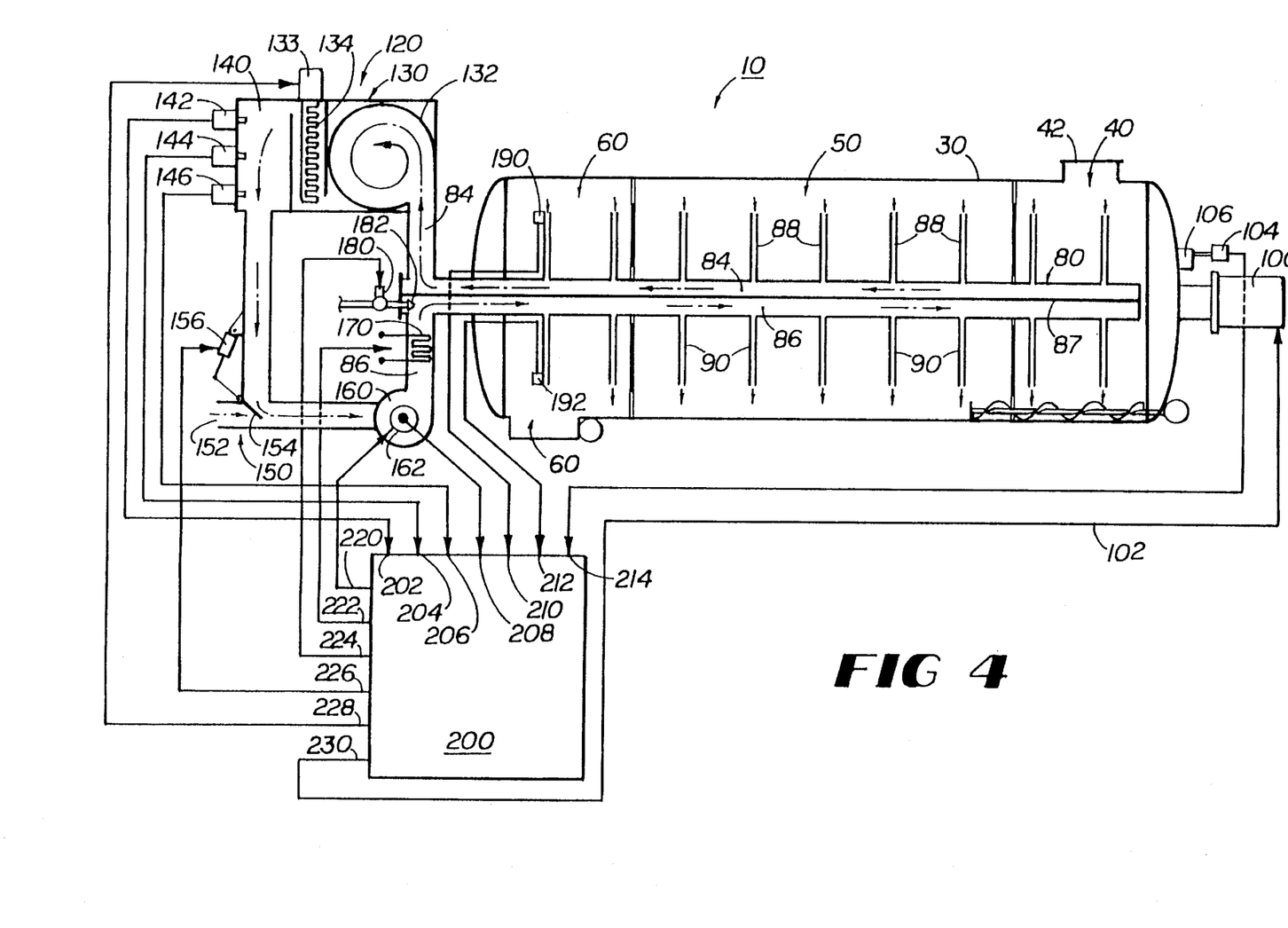
FIG. 4 is a schematic representation of a control system in conjunction with the reactor enclosure in accordance with the first embodiment of the present invention.

FIG. 4 is a schematic diagram showing one preferred embodiment of the environmental control system 120 in accordance with the present invention. Generally, a computer 200 controls the environmental parameters within the enclosure 31. Any general purpose digital computer would work if fitted with suitable interface electronics (such as an IBM-compatible PC fitted with an IEEE-488 bus). An embedded microprocessor could be used, as well as a dedicated industrial process control computer. Manual control could also be employed in some embodiments.

Rotation of the housing 30 is caused by the motor 100. The computer 200 has a motor speed control output 230 which sends an activation signal via a speed control line 102 to the motor 100. A limit switch 104 is disposed in fixed relation to the rotating housing 30 and engages a detent 106 affixed to the housing each time the detent 106 passes by the switch 104 causing it to generate pulses to a position signal input 214 to the computer 200 that can be used by the computer both to determine the rotational speed of the housing 30 and to determine position of the receiving hatch 42.

The computer 200 also generates a dehumidifier activation control output 228 which activates the compressor of the heat exchanger/dehumidifier 134. Control of the heat exchanger/dehumidifier 134 is based on three sensor inputs to the computer: an air temperature input 210 which receives a signal from an air temperature transducer 190 disposed in the enclosure 31; a pile temperature input 212 which receives a signal from a pile temperature transducer 192 disposed in the enclosure 31; and the humidity input 206 which receives a signal from the humidity sensor 146 in the air sensing chamber 140. When the computer 200 determines that humidity needs to be removed from the air, or that the air is too hot, it activates the heat exchanger/dehumidifier compressor 133 via a dehumidifier control output 228. Similarly, if the temperature is too low, the computer generates a heater control output 222 that activates a series of heating coils 170 placed in front of the blower 160.

Information from the humidity 146 sensor is used to control the addition of water as well. When water is to be added to the system, the computer 200 generates a water spray control output 224 that opens a solenoid-controlled water valve 180 which allows water to pass through a spray nozzle 182 into the air manifold 86.

The $O_2$ sensor 142 generates an $O_2$ sensor input 202 and the $CO_2$ sensor 144 generates a $CO_2$ sensor input 204 to the computer, which generates an $O_2$-add control signal 226 when the oxygen level falls below, or the carbon dioxide level falls above, the value necessary for decomposition of the particular type of material being composted. In one embodiment, oxygen is added when the $O_2$-add control signal 226 activates a new air assembly 150, which comprises a solenoid 156 which opens a valve 154 at an air intake 152, allowing fresh air to pass into the blower 160. In alternative embodiments, a compressed air or oxygen system could be employed in the new air assembly 150. Similarly, $CO_2$ can be removed from the system by opening a vent. This could be done using the new air assembly 150 as a discharge vent, rather than as an intake.

The air flow rate through the system is controlled by the computer 200 generating a blower speed control output signal 220 that activates the blower 160. The blower 160 may have a revolution encoder 164 which generates a blower speed feedback input 208 to the computer 200.

If desired, the computer 200 could also display sensory and process control information. This information could be displayed with analog means if computer control is not used in the particular embodiment being employed.

Although environmental control of the above embodiment is performed by a digital computer, it should be appreciated that some, or all, of the above-mentioned parameters could be controlled either manually or by analog electrical means. The decision as to which method of control to be employed for any parameter depends on the particular application involved. It should also be appreciated that, depending on the application, it may not be necessary to control all of the above parameters. It should also be appreciated that additional parameters might need to be controlled in certain applications. It should also be appreciated that the selection of the parameters to be controlled would be obvious to one skilled in the art.

In operating the present invention, certain additional reactants may have to be added to the material in order to achieve the desired result. Also, it may be necessary to add solidifiers (e.g. sawdust) to certain materials (e.g. municipal waste) to maintain the material at the proper consistency for decomposition.

Although the above embodiment of the present invention is designed especially to compost municipal waste, it should be appreciated that the present invention could be easily configured to decompose other types of material, such as agricultural waste, silage, timber waste and the like. The present invention could also be employed to reclaim polluted soil and other polluted materials.

Figure 5:
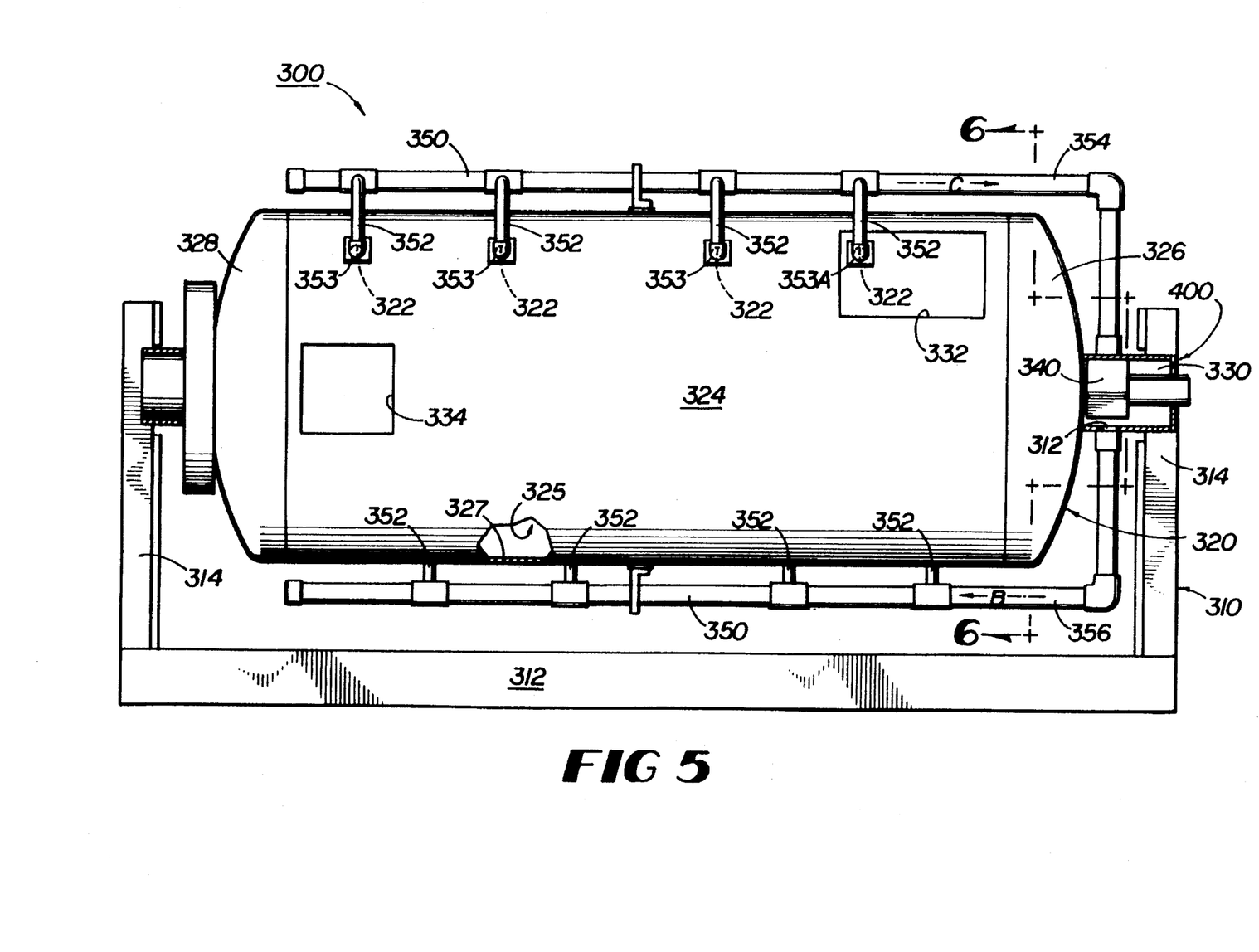
FIG. 5 is a side elevational view of a reaction vessel in accordance with a second embodiment of the present invention.

As shown in FIG. 5, an alternate preferred embodiment of the present invention 300 employs a substantially airtight housing 320 having a first outside surface 324 and a first inside surface 327 defining an enclosure 325 therein. The housing 320 also defines a plurality of openings 322 passing therethrough. The housing 320 has a first end 326 and a second end 328 and is rotatably mounted on a frame 310 comprising a base 312 and two oppositely disposed upright members 314 that act as load-bearing structure. The first end 326 defines a first aperture 332 for receiving the material into the enclosure 325, and the second end 328 defines a second aperture 334 for discharging the material from the enclosure 325.

A first air header 340 and a second air header 330 are disposed adjacent the first end 326. A plurality of air manifolds 350 are disposed external to the housing 320 and are in fluid communication with the enclosure 325 through the openings 322 defined by the housing 320 via a plurality of connectors 353 in fluid communication with a plurality of flexible air tubes 352. Using flexible air tubes 352 to connect the connectors 353 to the manifolds 350 has the advantages of reducing the precision required to make the connections as well as allowing a connector 353A to be placed on the first aperture 332, allowing the first aperture 332 to be opened without having to disconnect the connector 353A from the manifold 350.

The plurality of air manifolds 350 include a first plurality of air manifolds 356 in fluid communication with the first air header 340 and a second plurality of air manifolds 354 in fluid communication with the second air header 330. Air passes from the first air header 340 through the first plurality of air manifolds 356 into the enclosure 325 and passes out of the enclosure 325 through the second plurality of manifolds 354 to the second air header 330.

Figure 6:
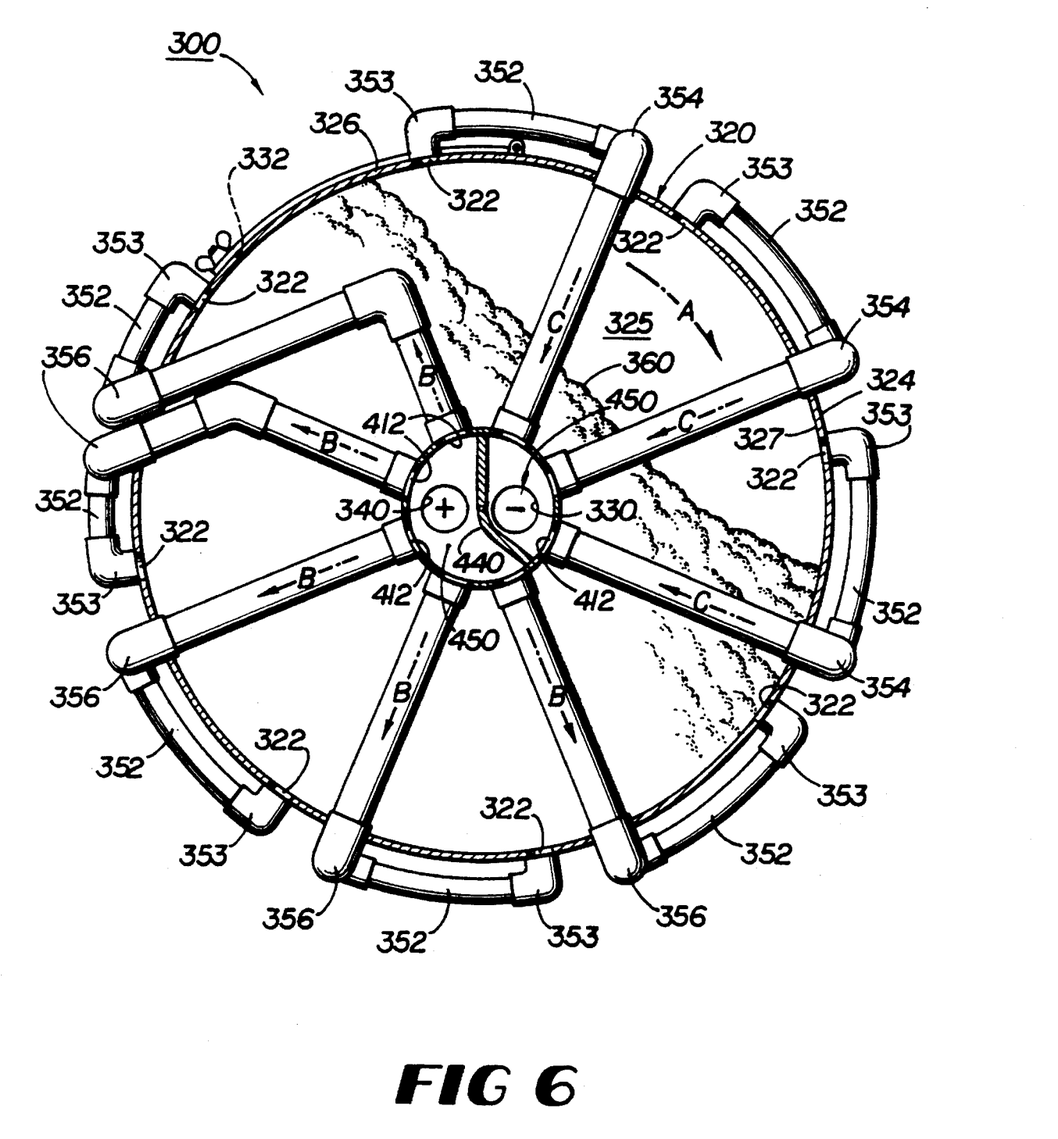
FIG. 6 is an end elevational view taken along line 6—6 in FIG. 5 of a reaction vessel, in accordance with the second embodiment of the present invention.

As shown in FIG. 6, the housing 320 rotates in the direction of arrow A, with air flowing into the enclosure 325 in the direction of arrows B through the first plurality of air manifolds 356. Once in the enclosure 325, the air circulates through the material 360 inside the enclosure 325 and exits through the second plurality of air manifolds 354 in the direction of arrows C.

In this embodiment there are no air tubes protruding into the composting material 360, therefore this embodiment eliminates problems associated with air tubes being broken by large clumps of matter. Furthermore, since the air manifolds 350 are external to the enclosure 325, they may be made of inexpensive materials such as polyvinyl chloride (PVC) tubing and can be repaired easily without having to access the inside of the enclosure 325. Other suitable materials for the air manifolds 350 include chlorinated polyvinyl chloride (CPVC) tubing. Although CPVC tubing is more expensive than PVC tubing, it withstands acidic chemicals better than PVC and could be used when composting material with high concentrations of caustic chemicals.

Figure 7:
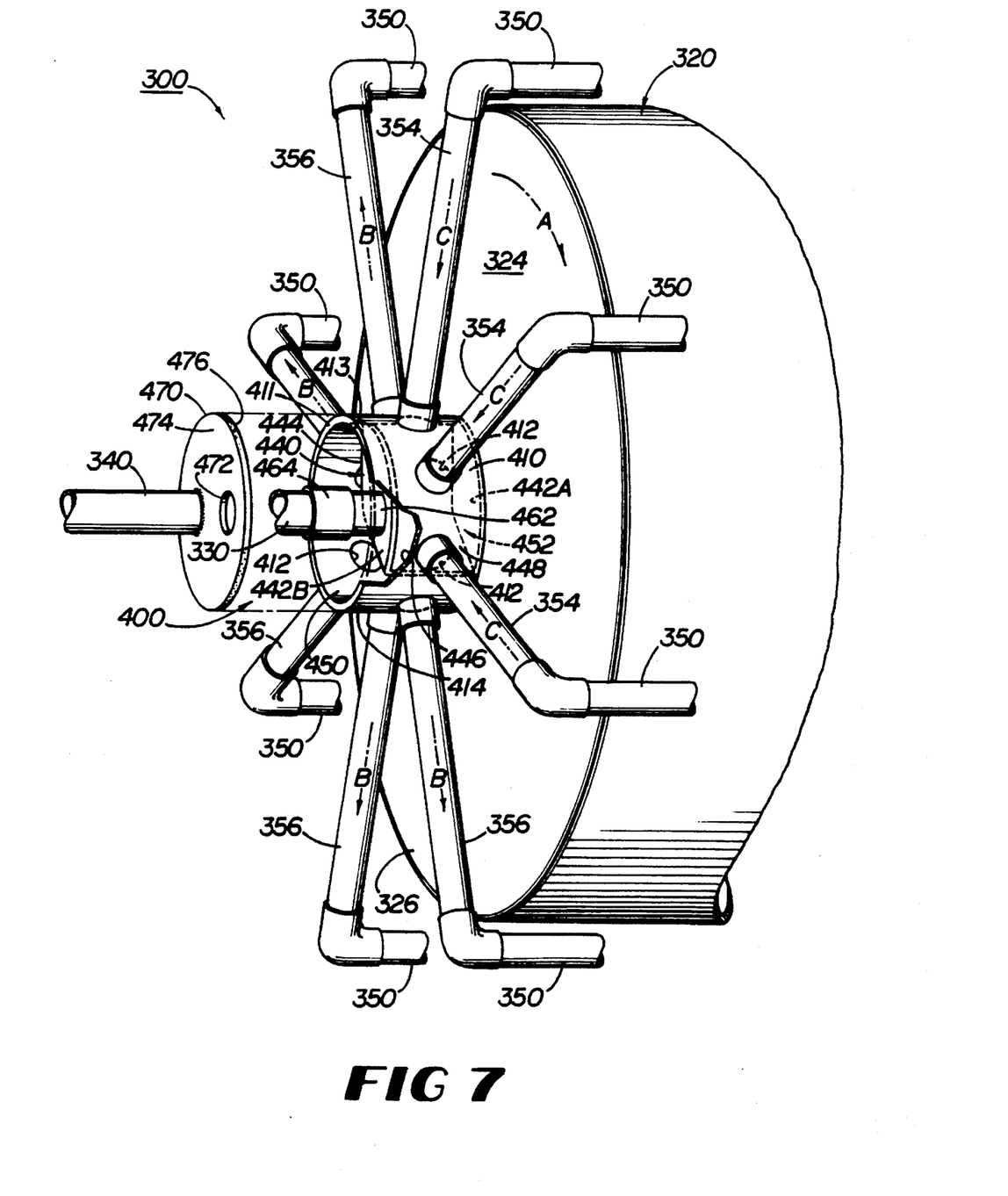
FIG. 7 is a top front exploded perspective view of the first end of a second embodiment of the present invention.

As shown in FIG. 7, a means 400 is provided for selectively directing fluid flow from the first header 340 through the first plurality of manifolds 356 and for selectively directing fluid flow from the second plurality of manifolds 354 through the second header 330. The ones of the plurality of air manifolds 350 included in the first plurality of manifolds 356 and second plurality of manifolds 354 depends on the rotational position of the housing 320.

The directing means 400 comprises a tubular member 410 that extends axially from the first outside surface 324 of the housing 320 adjacent the first end 326 and terminates in an end 411. The tubular member 410 has a second inside surface 413 and a second outside surface 414 and defines a plurality of orifices 412 therethrough spaced apart about the circumference of tubular member 410. An air manifold 350 extends radially from each of the orifices 412.

A partitioning member 440 is disposed within the tubular member 410 and has two oppositely disposed upright plates 442A and 442B connected by a curved member 444 having a third inside surface 446 and a third outside surface 448. The partitioning member 440 defines a first chamber 452 between the third inside surface 446 of the curved member 444, the two upright plates 442A and 442B and the second inside surface 413 of the tubular member 410. Extending from upright plate 442B is a tube 462 in fluid communication with the second chamber 452 and connected to the second air header 330 via a flexible tube 464. Thus the second plurality of air manifolds 354 are in fluid communication with the second air header 330 via the second chamber 452. The tube 462 may be located near the bottom of the second chamber 452 to facilitate removal of condensed water or debris in the second chamber 452 via the second air header 330.

A stationary wall 470, having a first side 474 and a second side 476, covers the end 411 of the tubular member 410. A first chamber 450 is defined by the second side 476 of the wall 470, the third outside surface 448 of the curved member 444 and the second inside surface 413 of the tubular member 410, with first chamber 450 in fluid communication with the first air header 340. Thus, the first plurality of air manifolds 356 is in fluid communication with the first chamber 450 and the first air header 340.

The positive pressure of incoming air from the first air header 340 and the negative air pressure of the air going out of the second air header 330 acts to push the partitioning member 440 firmly against the second inside surface 413 of the tubular member 410. As the housing 320 rotates in the direction of arrow A, the position of the partitioning member 440 remains substantially fixed relative to the wall 470. The tubular member 410 and the air manifolds 350, on the other hand, rotate around the partitioning member 440. Therefore, because the partitioning member 440 is affixed to the second air header 330 via a flexible tube 464, the partitioning member 440 is able to act as a valve in concert with the orifices 412 in the tubular member 410. A plastic strip (not shown) may be affixed to the edge of the partitioning member 440 to act as a valve gasket against the second inside surface 413, thereby reducing air leakage.

Figure 8A:
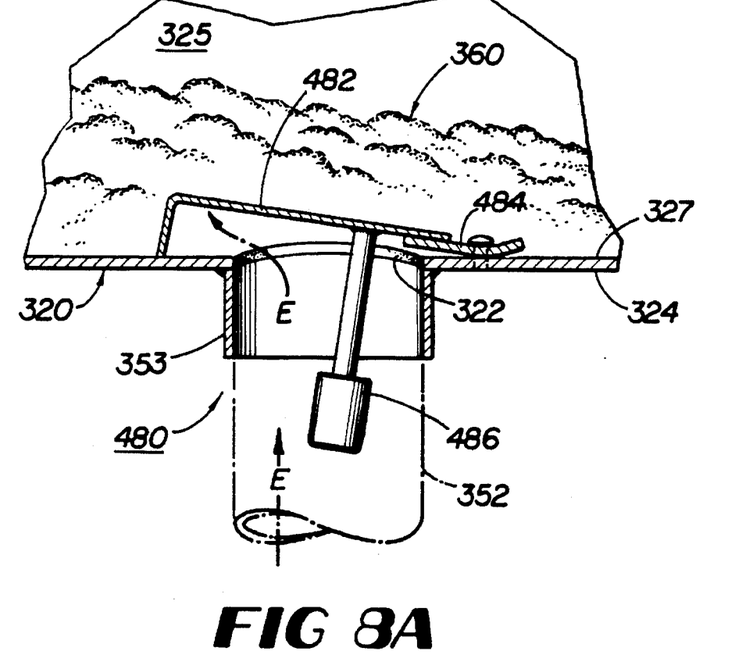
FIG. 8A is a side elevational view of an air port in the exhaust position.
Figure 8B:
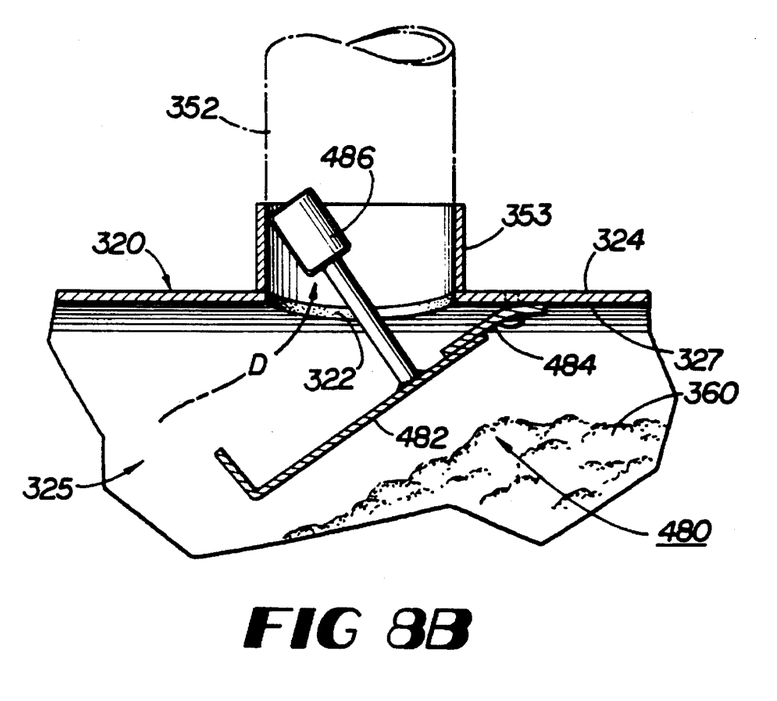
FIG. 8B is a side elevational view of an air port in the intake position.

As shown in FIGS. 8A and 8B, disposed adjacent each one of the openings 322 is a means 480 for preventing the material 360 from entering the plurality of air manifolds 350 while allowing air to pass therethrough. Each one of the preventing means 480 comprises a first member 482, attached to the inside surface 327 of the housing 320 adjacent the opening 322 by a hinge 484. As shown in FIG. 8A, the first member 482 is has a first position in which the first member 482 substantially covers the opening 322 so as to prevent the material 360 from falling into the opening 322 while allowing air under pressure to enter the enclosure 325 in the direction of arrow E through the opening 322. As shown in FIG. 8B, the first member 482 also has a second position in which the first member 482 is partially disposed away from the opening 322 thereby allowing air to exit the enclosure 325 in the direction of arrow D. A second member 486 extending perpendicularly away from the first member 482 and partially disposed within the opening 322 may be used to limit the distance of the first member 482 from the opening 322 while the first member 482 is in the second position. As would be obvious to one skilled in the art, the preventing means 480 could comprise other embodiments, including a mesh (not shown) or a screen (not shown) covering each of the openings.

The above embodiments are given as illustrative examples and are not intended to impose any limitations on the invention. It will be readily appreciated that many deviations may be made from the specific embodiments disclosed in this specification without departing from the invention. Accordingly it is intended to cover all such modifications as within the scope of this invention.

What is claimed is:

1. An apparatus for biologically decomposing a material, comprising:

a. a frame;

b. a substantially airtight housing rotatably mounted on said frame, said housing having a first outside surface and a first inside surface, a first end and a second end, the first inside surface defining an enclosure therein, the housing defining a plurality of openings therethrough;

c. a first air header;

d. a second air header;

e. a plurality of air manifolds disposed external to said housing and in fluid communication with the enclosure through the openings defined by said housing, said plurality of air manifolds including:

i. a first plurality of air manifolds in fluid communication with said first air header; and ii. a second plurality of air manifolds in fluid communication with said second air header; and f. a means for selectively directing fluid flow such that air passes from said first air header through said first plurality of air manifolds into the enclosure and passes out of the enclosure through said second plurality of manifolds to said second air header.

2. The apparatus of claim 1, wherein the first end defines a first aperture for receiving the material into the enclosure and the second end defines a second aperture for discharging the material from the enclosure.

3. The apparatus of claim 1, wherein said means directs fluid flow from said first header through said first plurality of manifolds and for selectively directing fluid flow from said second plurality of manifolds through said second header, the ones of said plurality of air manifolds included in said first plurality and said second plurality depending on the rotational position of said housing.

4. The apparatus of claim 3 wherein said directing means comprises:

a. a tubular member, extending axially from the first outside surface of said housing, having a second inside surface and a second outside surface and defining a plurality of orifices therethrough spaced apart about the circumference of said tubular member, one of said manifolds extending radially from each of the orifices, said tubular member terminating at an end;

b. a partitioning member disposed within the tubular member having two oppositely disposed upright plates connected by a curved member having a third inside surface and a third outside surface, said curved member being perpendicular to the axis of said housing, said partitioning member defining a second chamber between said third inside surface of said curved member, said two upright plates and said second inside surface of said tubular member, said second chamber being in fluid communication with said second air header; and c. a wall, having a first side and a second side, covering the end of said tubular member, a first chamber being defined by the second side of said wall, said third outside surface of said curved member and said second inside surface of said tubular member, said first chamber being in fluid communication with said first air header, such that said first plurality of air manifolds is in fluid communication with the first chamber and said second plurality of air manifolds is in fluid communication with the second chamber.

5. The apparatus of claim 1 further comprising means, disposed adjacent each one of said plurality of openings, for preventing the material from entering said plurality of air manifolds while allowing air to pass therethrough.

6. The apparatus of claim 6 wherein each one of said preventing means comprises a first member, hingedly attached to said inside surface adjacent said opening, moveable between a first position, in which said first member substantially covers the opening so as to prevent the material from falling into the opening while allowing air under pressure to enter said enclosure through the opening, and a second position in which said first member is partially disposed away from the opening, thereby allowing air to exit said enclosure.

7. The apparatus of claim 7 further comprising a second member extending perpendicularly away from said first member and partially disposed within the opening so as to limit the distance of said first member from the opening while said first member is in the second position.

8. The apparatus of claim 6 wherein said preventing means comprises a mesh coveting each of the openings.

9. The apparatus of claim 6 wherein said preventing means comprises a screen covering each of the openings.

10. The apparatus of claim 1 wherein said air manifolds comprise polyvinyl chloride tubing.

11. The apparatus of claim 1 wherein said air manifolds comprise chlorinated polyvinyl chloride tubing.

12. The vessel of claim 1 further comprising means for agitating the material in the enclosure.

13. The vessel of claim 12 wherein said agitating means comprises a motor, coupled to said housing and said frame, that rotates said housing.

14. An apparatus for biologically decomposing a material, comprising:

a. a frame;

b. a substantially airtight housing rotatably mounted on said frame, said housing having a first outside surface and a first inside surface, the first inside surface defining an enclosure therein, the housing defining a plurality of openings therethrough, a first end defining a first aperture for receiving the material into the enclosure and a second end defining a second aperture for discharging the material from the enclosure;

c. a first air header;

d. a second air header;

e. a plurality of air manifolds disposed external to said housing and in fluid communication with the enclosure through the openings defined by said housing, said plurality of air manifolds including:

i. a first plurality of air manifolds in fluid communication with said first air header, wherein air passes from said first air header through said first plurality of air manifolds into the enclosure; and ii. a second plurality of air manifolds in fluid communication with said second air header, wherein air passes out of the enclosure through said second plurality of manifolds to said second air header;

f. a tubular member, extending axially from the first outside surface of said housing, having a second inside surface and a second outside surface and defining a plurality of orifices therethrough spaced apart about the circumference of said tubular member, one of said manifolds extending radially from each of the orifices, said tubular member terminating at an end;

g. a partitioning member disposed within the tubular member having two oppositely disposed upright plates connected by a curved member having a third inside surface and a third outside surface, said curved member being perpendicular to the axis of said housing, said partitioning member defining a second chamber between said third inside surface of said curved member, said two upright plates and said second inside surface of said tubular member, said second chamber being in fluid communication with said second air header; and h. a wall, having a first side and a second side, covering the end of said tubular member, a first chamber being defined by the second side of said wall, said third outside surface of said curved member and said second inside surface of said tubular member, said first chamber being in fluid communication with said first air header, such that said first plurality of air manifolds is in fluid communication with the first chamber and said second plurality of air manifolds is in fluid communication with the second chamber.

15. The apparatus of claim 14 further comprising:

a. a plurality of first members disposed adjacent each one of said plurality of openings, each of said first members being hingedly attached to said inside surface adjacent said opening and moveable between a first position, in which said first member substantially covers the opening so as to prevent the material from falling into the opening while allowing air under pressure to enter said enclosure through the opening, and a second position in which said first member is partially disposed away from the opening, thereby allowing air to exit said enclosure; and b. a plurality of second members, each of said second members being extending perpendicularly away from said first member and partially disposed within the opening so as to limit the distance of said first member from the opening while said first member is in the second position.

16. The apparatus of claim 14 wherein said air manifolds comprise polyvinyl chloride tubing.

17. The apparatus of claim 14 further comprising a motor, coupled to said housing and said frame, that rotates said housing thereby agitating the material in the enclosure.

\* \* \* \* \*